United States Patent [19]
Farin et al.

[11] Patent Number: 5,267,997
[45] Date of Patent: Dec. 7, 1993

[54] HIGH-FREQUENCY ELECTROSURGERY APPARATUS WITH LIMITATION OF EFFECTIVE VALUE OF CURRENT FLOWING THROUGH A SURGICAL INSTRUMENT

[75] Inventors: Günter Farin, Tübingen; Reiner Mausberg; Heiko Visser, both of Göttingen; Karl Fastenmeier, München; Georg Lohr, Ottobrunn, all of Fed. Rep. of Germany

[73] Assignee: Erbe Elektromedizin GmbH, Tubingen, Fed. Rep. of Germany

[21] Appl. No.: 821,412

[22] Filed: Jan. 15, 1992

[30] Foreign Application Priority Data

Jan. 16, 1991 [EP] European Pat. Off. ... EP91100442.2

[51] Int. Cl.⁵ ............................................. A61B 17/39
[52] U.S. Cl. ....................................................... 606/38
[58] Field of Search ...................................... 606/37–40; 128/908, 421, 804

[56] References Cited

U.S. PATENT DOCUMENTS

| | | | |
|---|---|---|---|
| 3,886,932 | 6/1975 | Suessmilch | 128/908 |
| 4,741,334 | 5/1988 | Irnich | 128/908 |

FOREIGN PATENT DOCUMENTS

| | | | |
|---|---|---|---|
| 341446 | 8/1990 | European Pat. Off. | |
| 3228136 | 9/1984 | Fed. Rep. of Germany | 606/37 |
| 2417303 | 9/1979 | France | |
| 2213381A | 8/1989 | United Kingdom | |

*Primary Examiner*—Lee S. Cohen
*Assistant Examiner*—Marianne Parker
*Attorney, Agent, or Firm*—Frishauf, Holtz, Goodman & Woodward

[57] ABSTRACT

A high-frequency electrosurgery apparatus for cutting and/or coagulating biological tissues that may have a number of operating modes is described. As control panel on which one or more parameters of the high-frequency output of the apparatus can be set. Particularly important is the current-limiting system which includes setting of a desired maximal current level, to which for a particular mode of operation the current can be limited or in response to which a warning signal may be activated and/or the high-frequency generator shut down. The effective current that the application instrument reaches or exceeds previously set maximal current level. In such a high-frequency electrosurgery apparatus the cable leading to the active electrode is provided with electrial shielding which is connected to the conductor leading to the neutral electrode at a location between the output transformer of the apparatus and the current sensor of the current limiting system.

22 Claims, 8 Drawing Sheets

HIGH-FREQUENCY ELECTROSURGERY APPARATUS WITH LIMITATION OF EFFECTIVE VALUE OF CURRENT FLOWING THROUGH A SURGICAL INSTRUMENT

This invention concerns a high-frequency electrosurgery device for cutting and/or coagulating biological tissue having at least one mode of operation, having a manually positionable instrument typically used for electrosurgery, which applies electric to biological tissues, and also having a suitable control panel for setting at least one parameter of the high-frequency output of the apparatus.

A known problem of high-frequency electrosurgery is the reproducibility and constancy of the quality of cutting operations, tissue coagulating procedures and operations of both cutting and tissue coagulation in a surgical procedure. It is also know that the quality of cutting and coagulation procedures using electrosurgery apparatus heretofore available is dependent upon magnitude of the high-frequency voltage or the intensity of an electric arc between electrode and tissue used with the. See G. Lux and L. Semm "Hochfrequenzdiathermie in der Endoskopie", Springer-Verlag, Berlin and Heidelberg, 1987, pp. 33ff and 149ff.

for decades high-frequency electrosurgery apparatus was used which also found application in dentistry. The reproducibility of the quality of cutting and/or coagulation procedures performed with automatically regulated high-frequency generators was in recent years distinctly improved in comparison to high-frequency operators not automatically regulated. Thus, for example, high-frequency electrosurgery apparatus has become known from U.S. Pat. No. 4,092,986 as well as from German Patent 02 85 962 in which the output voltage is automatically maintained constant. From German Published Patent Application 25 04 280 and from European Patent 0 219 568, high-frequency electrosurgery apparatus has become known which are equipped with automatic regulation circuits which regulate at a constant value the intensity of electric arcs between an active electrode and living tissue.

SUMMARY OF THE INVENTION

The invention concerns particularly an improvement of high-frequency electrosurgery apparatus with automatic regulation of the output voltage and/or the intensity of an electric arc between an active electrode and living tissue. The improvement is advantageously applicable also to procedures of dentistry with other known high-frequency electrosurgery apparatus lacking the above-mentioned kind of automatic HF voltage regulation.

It is an object of the present invention to improve the utility of high-frequency electrosurgery devices for purposes of dentistry in a manner which will assure by operating the apparatus in the simplest possible way for avoidance of unintended damage to living tissue to the greatest intent possible.

Briefly, an electric-current-limiting system having accessible controls for setting a maximal current level for the surgical instrument which applies current, as an active electrode, to a patient's tissue is provided for detecting the presence of current exceeding that maximal value. In response to such excess current, the high-frequency generator is shut off, or a warning signal is produced, or both the generator shut-off and the warning signal are produced. The same current limiting system may also serve to prevent excess current value from arising in some cases. More particularly, the high-frequency electrosurgery equipment may have several modes of operation, so that the current limiting system may advantageously provide different ways, depending upon the mode of operation, for limiting a high-frequency current caused to flow in the patient's tissue. Different settings for the above-mentioned maximal current value can be internally provided according to a mode of operation that is externally selected.

The invention is based on the recognition that even in the case of a relatively short-duration contact of a surgical instrument with, for example, a tooth filling of gold a current flow can happen that quickly produces damage to the pulpa tissue. Such damage often cannot be noticed at the time either by the dentist or by the patient. Damage of the pulpa tissue by electrical contact of an active electrode with a gold filling or with other metallic materials used in dentistry can occur in that way because with all heretofore known high-frequency electrosurgery apparatus, in such cases an excessively great HF current can flow through the root canal of a tooth.

By means of comparison experiments on animals it has been possible to establish, by tests on pig teeth filled with amalgam or crowned with gold crowns, that distinct increases of current during cutting and/or coagulation procedures arose in the use of known high-frequency electrosurgery apparatus as soon as the active electrode came into contact with an amalgam filling or a gold crown, whereas under otherwise identical conditions with the use of a high-frequency electrosurgery apparatus of the invention, such current increases did not take place.

A current limiting system in a high-frequency electrosurgery apparatus of the present invention consists, for example, of a current monitor, which delivers a first electric signal isproportional to the high-frequency current in the application instrument, a limiting value signal source for which the limiting value can be set, which produces a second electrical signal a which is proportional to the maximal current level set therein and a comparator which from a ratio of the first to the second electrical signal produces an electric control signal that is supplied to the power supply for the high-frequency generator or directly to the high-frequency generator of the electrosurgery apparatus and is also supplied for a device that produces a warning signal. The control signal may be used to limit the high-frequency current to the maximal level that has been set, or to shut off the high-frequency generator and/or activate warning signal generator. The current monitor can for example be inserted in the secondary or in the primary current circuit of the output transformer which is usually present in high-frequency electrosurgical apparatus.

In the design and construction of the current monitor, attention is particularly important to the fact that only the work component of the high-frequency electrical alternating current in the application instrument is of interest with reference to the thermal effects of the current, so that for example a phase-selective rectifier should be used. Since the capacitive component of the high-frequency electric alternating current in the application instrument arises from stray capacitances of components, connectors and cables, it is possible by suitable design of the application instrument to reduce this capacitive component to a minimum. This result can be obtained, for example, if the cable leading to the active electrode is electrically shielded and this shielding is connected within the high-frequency electrosurgical apparatus along with the conductor leading to the neutral electrode, to ground potential, as is described further below with reference to an illustrative embodiment.

In addition, care should be taken, especially in the case of amplitude modulated HF current, that the electric output signal i of the current monitor should correspond to a current-time integral which is compatible with the heat capacity of the thermally loaded tissue volume. This means that preferably the effective value, or the quadratic mean, of the more or less amplitude-modulated high-frequency alternating current, which varies more or less from the sinusoidal form, must be taken into account.

In a further development of the invention, the high-frequency electrosurgery apparatus is further equipped with a display on where the maximal current magnitude level that has been set for the operation of the apparatus is displayed.

If a high-frequency electrosurgery apparatus has the capability of operating in two or more modes of operation, for example the cutting mode in which a cut is made that is free of coagulation effect, another cutting mode that coagulates and/or various coagulation modes such as soft coagulation, forced coagulation or spray coagulation, it is possible to allocate a separate current limiting circuit in the current limiting system and/or a separate provision for setting a maximal current magnitude level in the high-frequency electrosurgical apparatus.

DRAWINGS

The invention is further described by way of illustrative example with reference to the annexed drawing, in which.

DESCRIPTION OF THE ILLUSTRATED EMBODIMENTS

Figure 1:
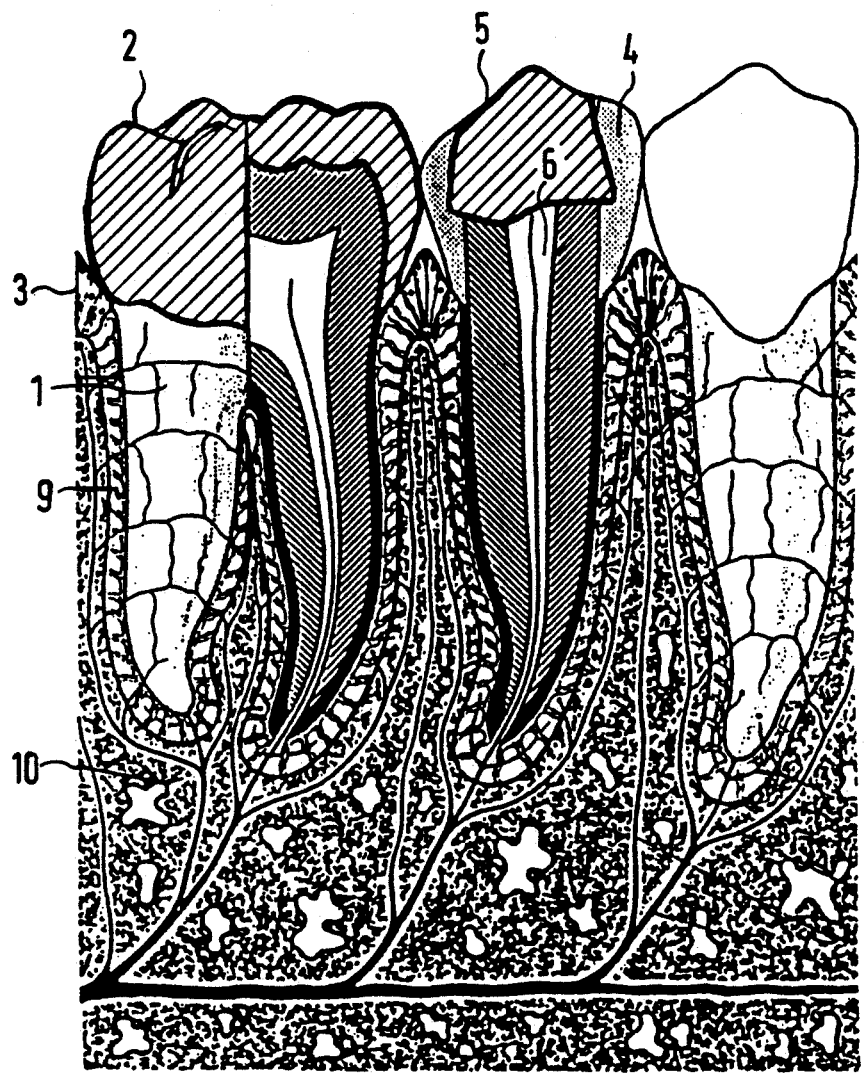
FIG. 1 is a schematic representation of the cross section of a set of teeth.
Figure 2:
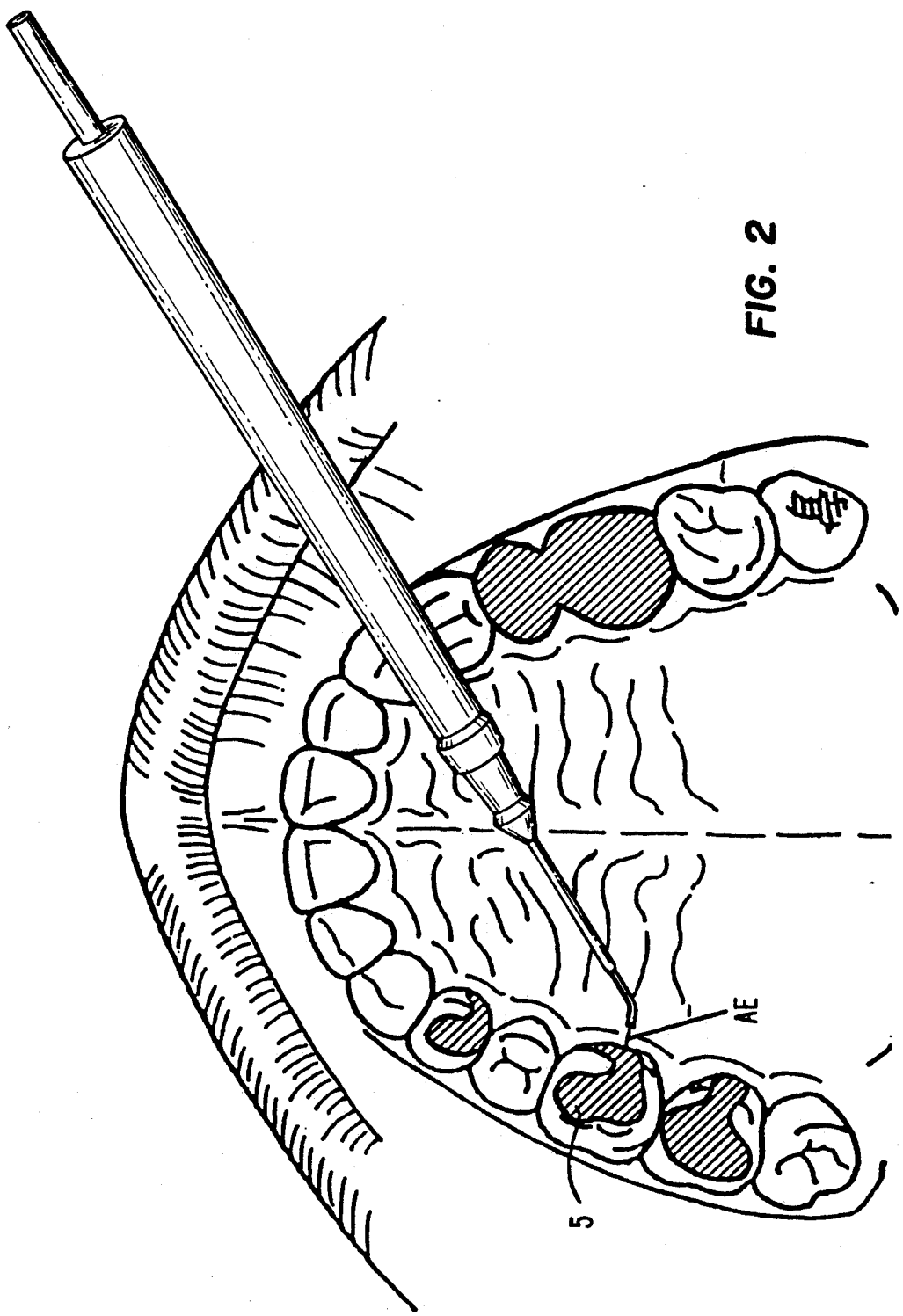
FIG. 2 is a top view of a denture or set of teeth, to one tooth of which the tip of an active electrode is applied.

FIG. 1 schematically shows a section of a set of teeth in which the tooth 1 is crowned, for example, with an electrically conducting crown 2 which touches the gums 3. The tooth 4 is filled with an electrically conducting filling 5, for example an amalgam filling which touches the pulpa 6 of the tooth. If the active electrode AE of a high-frequency electrosurgery apparatus as shown in FIG. 2 touches an amalgam filling 5, electrical current can flow through the amalgam filling into the pulpa, as the result of which the pulpa tissue can be thermally destroyed within a short time. The pulpa tissue is important for the vitality and the reaction capability of a tooth. A dentist performing an operation with an electrosurgery apparatus does not notice this complication because the pulpa tissue is located inside the tooth.

If the active electrode AE of a high-frequency electrosurgery apparatus such as is shown in FIG. 2 touches a gold crown, which as a rule is in electrically conducting contact with the gum, an electrical current can flow through the gold crown into the adjacent gum and destroy part of the gum thermally in a short time. It can be assumed that the electrical current in this case will flow preferably through the tooth ligament and destroy that thermally. The tooth ligament is a fiber-rich, dense ligament which holds the root of the tooth in the jaw bone. It is the holding apparatus of a tooth. The operating dentist does not notice this complication because the tooth ligament is not visible in the relatively narrow gap between the root of the tooth and jaw bone 10.

Measurement of the current strength during the application of high frequency of electrosurgery of pig teeth filled with amalgam or crowned with gold crowns showed distinct current increases during cutting and/or coagulation procedures as soon as the active electrode AE touches amalgam fillings or gold crowns. The same complications can occur in human dentistry when the active electrode touches conductive clips, instruments, implants, etc. Similar complications can also occur in other surgical specialties and in fact normally when an active electrode touches parts having good electric conduction, of which the conductive surfaces in contact with the tissues of the patient is greater than the intended contact surface between active electrode and tissues of the patient.

Figure 3:
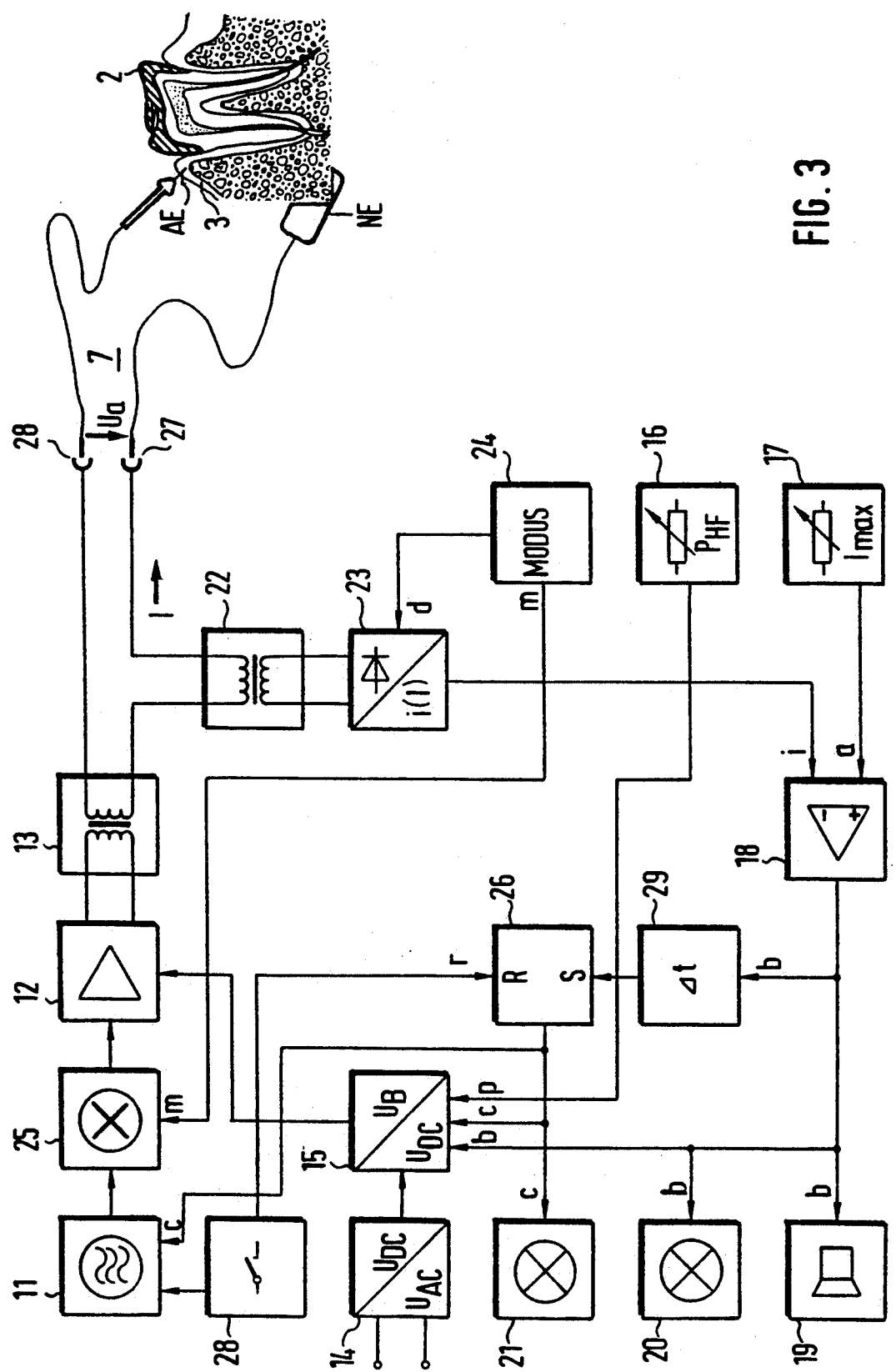
FIGS. 3 through 6 are circuit block diagrams of different embodiments of a high-frequency electrosurgery apparatus according to the invention.

In FIG. 3 the principle of a high-frequency surgergy apparatus according to the invention is represented in the form of a circuit block diagram. The high-frequency generator of this illustrative example corresponds in a general way to examples known in high-frequency electrosurgery apparatus. It consists of the elements which are in themselves known: high-frequency oscillator 11, amplitude modulator 25, high-frequency power amplifier 12, output transformer 13, power supply 14, 15 and power setting device 16 for the high-frequency output power $P_{HF}$. The setting of the high-frequency output power $P_{HF}$ is produced in the known high-frequency electrosurgery apparatus of the above-described kind, for example, by variation of the operating voltage $U_B$ by means of a suitable setting means 16. The high-frequency current I and the application rod 7 of such a high-frequency electrosurgery apparatus depends upon the voltage $U_A$ and the output 27, 28 of the apparatus, as well as upon the electrical resistance of the power circuit. The electrical resistance of the power circuit during cutting and/or coagulation procedures is determined mainly by the electrical transition resistance between the active electrode AE and biological tissue 3. This transition resistance is relatively large as a result of the relatively small contact surface between active electrode and tissue.

If the relatively small-surfaced active electrode AE, instead of touching the tissue 3 which is to be cut and/or coagulated, touches electrically conducting parts, as for example gold crowns, amalgam fillings 5 or metallic instruments, then as a result the contact surfaces of these electrically conducting parts which is relatively great in comparison with the tissue of the patient, a relatively smaller electrical resistance can be involved and thereby greater current I relative to the intended cutting and/or coagulating procedure. That current is capable of producing unintended thermal destruction of tissue.

For this reason the high-frequency electrosurgery apparatus corresponding to FIG. 3 is additionally provided with current limiting equipment 22, 23, 17, 18. Such current limiting equipment consists for example of a current sensor 22, 23 which forms an electrical signal $i = f(I)$ which is proportional to the current I in the application rod. This signal is supplied to a comparator 18, which supplies a control signal b to the power supply 15 when the signal $i = f(I)$ is equal to or greater than a reference signal $a = f(I_{max})$, wherein $I_{max}$ is the maximal value of a current I that can be set by a user at the setting device 17.

The signal b can either control the power supply 15 in such a way that I does not become greater than the maximal value $I_{max}$ or so that the operating voltage $U_B$ and/or the oscillator 11 is switched off at once or after a delay whenever I is equal or greater than $I_{max}$. The signal b can additionally be supplied to acoustic signal transducers 19 and/or optical transducers, which generate signals when I is equal or greater than $I_{max}$.

The delay $\Delta t$ of the signal b by means of the delay unit 29 is practical when the current I is intended to be greater than $I_{max}$ for a short time and/or when the operating voltage $U_B$ and/or the oscillator 11 must be switched off immediately, but only after a delay of $\Delta t$. This is advantageous, for example, in the initial cutting procedure, when the current I is switched on while the active electrode AE already touches the tissue, for in this situation it is known that for a short time a greater current is necessary than during the cutting procedure.

If the signal b ought to switch off the operating voltage $U_B$ and/or the oscillator 11 automatically after a delay, an RS flipflop is necessary in addition to the storage element 26. The RS flipflop delivers an electrical signal c when the signal b appears at the setting input S of the storage element 26. The signal c is supplied to the power supply 15 and/or to the oscillator 11 in order to shut down the operating voltage $U_B$ and/or the oscillator 11. The signal c continues to be maintained also after the disappearance of the signal b, until by renewed actuation of a switch 28, for example the finger or foot switch usually present for activating the oscillator, releases an electrical signal r to the reset input R of the storage element 26, which erases the signal c.

The signal c can supplementarily be supplied to an optical and/or acoustic signal producer 21.

If the high-frequency electrosurgery apparatus should have various operating modes, for example if the output voltage is more or less modulated in amplitude, in a further feature of the invention the demodulator 23 is supplied by a mode setting device 24 with an electrical signal d, which for example fits the integration time constant of the demodulator to the modulation selected in each case, so that the signal l for example is also proportional to the effective value of the current I when the output voltage is modulated more or less strongly in amplitude.

The modulation of the output voltage $U_a$ takes place by means of the signal m, which the mode setting device 24 generates and which for example is supplied to the amplitude modulator 25.

Figure 4:
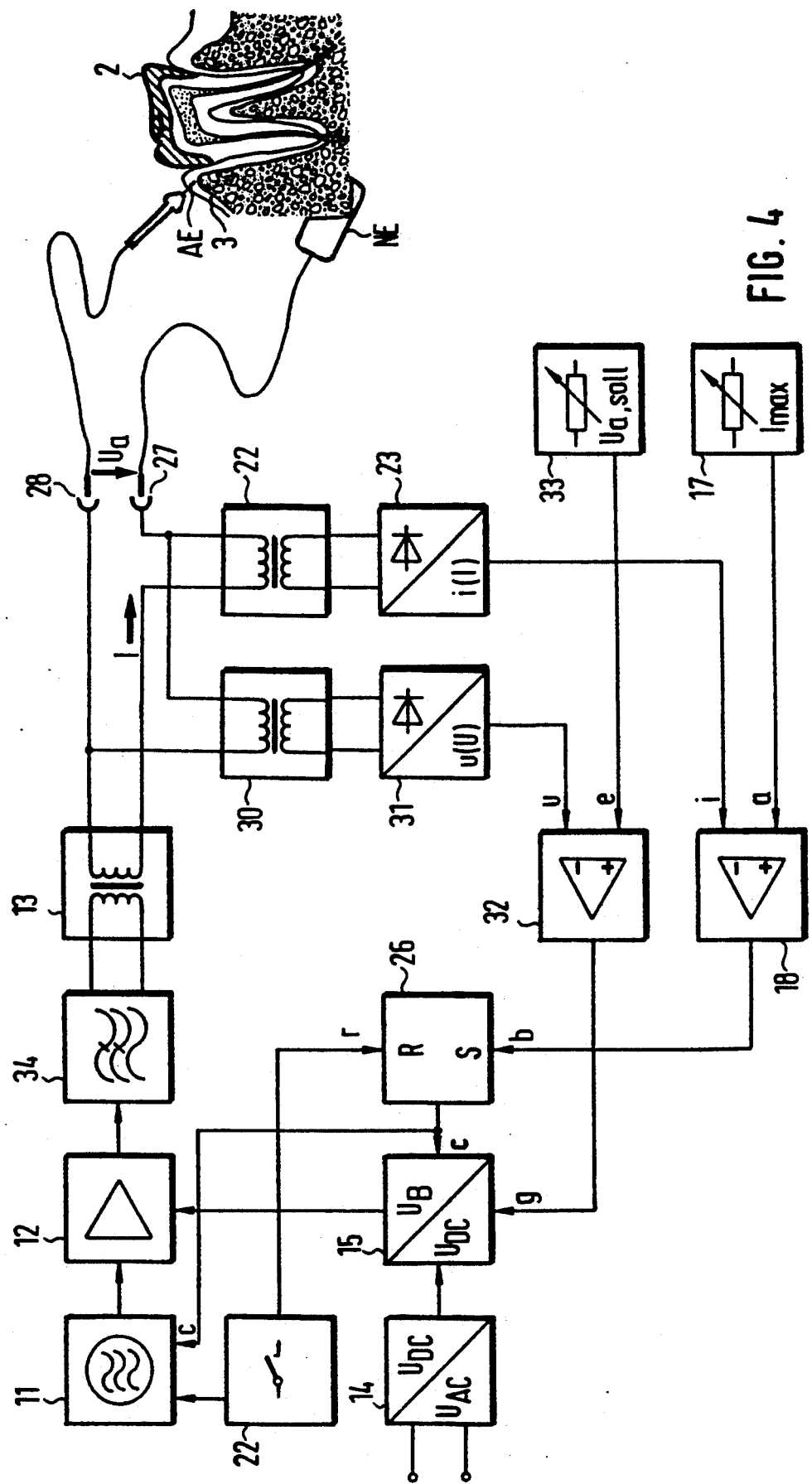

In FIG. 4 another embodiment of a high-frequency electrosurgery apparatus according to the invention is shown in the form of a circuit block diagram. The high-frequency generator of this illustrative example corresponds basically to the known high-frequency electrosurgery apparatus with automatic regulation of the high-frequency output voltage, for example as shown in European patent document A-0285 962. It consists of functional elements known in themselves and also shown in FIG. 3: high-frequency oscillator 11, high-frequency power amplifier 12, output transformer 13, power supply 14, 15 and, deviating from FIG. 3, a reference value source 33 for the high-frequency output voltage $U_{a-ref}$ at the output 27, 28 of the high-frequency electrosurgery apparatus. The automatic regulation of the HF output voltage $U_a$ takes place in a manner known in itself by means of a HF voltage sensor 30, 31, which delivers an electrical signal $u = f(U_a)$ which is proportional to the HF voltage $U_a$. This signal u is supplied to a comparator 12 where it is compared with a reference value signal e from the reference value source 33. The output signal g of the comparator 32 is supplied in a suitable way to the power supply 15 in order to control the operating voltage $U_B$ of the power amplifier 12 so that the HF output voltage $U_a$ corresponds to the value set into the reference value source 33. For the automatic regulation of the HF output voltage $U_a$ it is useful for the high-frequency generator to deliver a sinusoidal voltage as free as possible of harmonics: a low pass filter 34 is therefore interposed in circuit between the power amplifier 12 and the output transformer 13.

The current limiting device and all other functions of this illustrated embodiment correspond essentially to the embodiment shown in FIG. 3 and its description. Since high-frequency electrosurgery apparatus with automatic regulation of the HF output voltage $U_a$ usually have no amplitude modulation of the HF output voltage $U_a$, the elements 24 and 25 shown for this purpose in FIG. 3 are omitted in FIG. 4.

Figure 5:
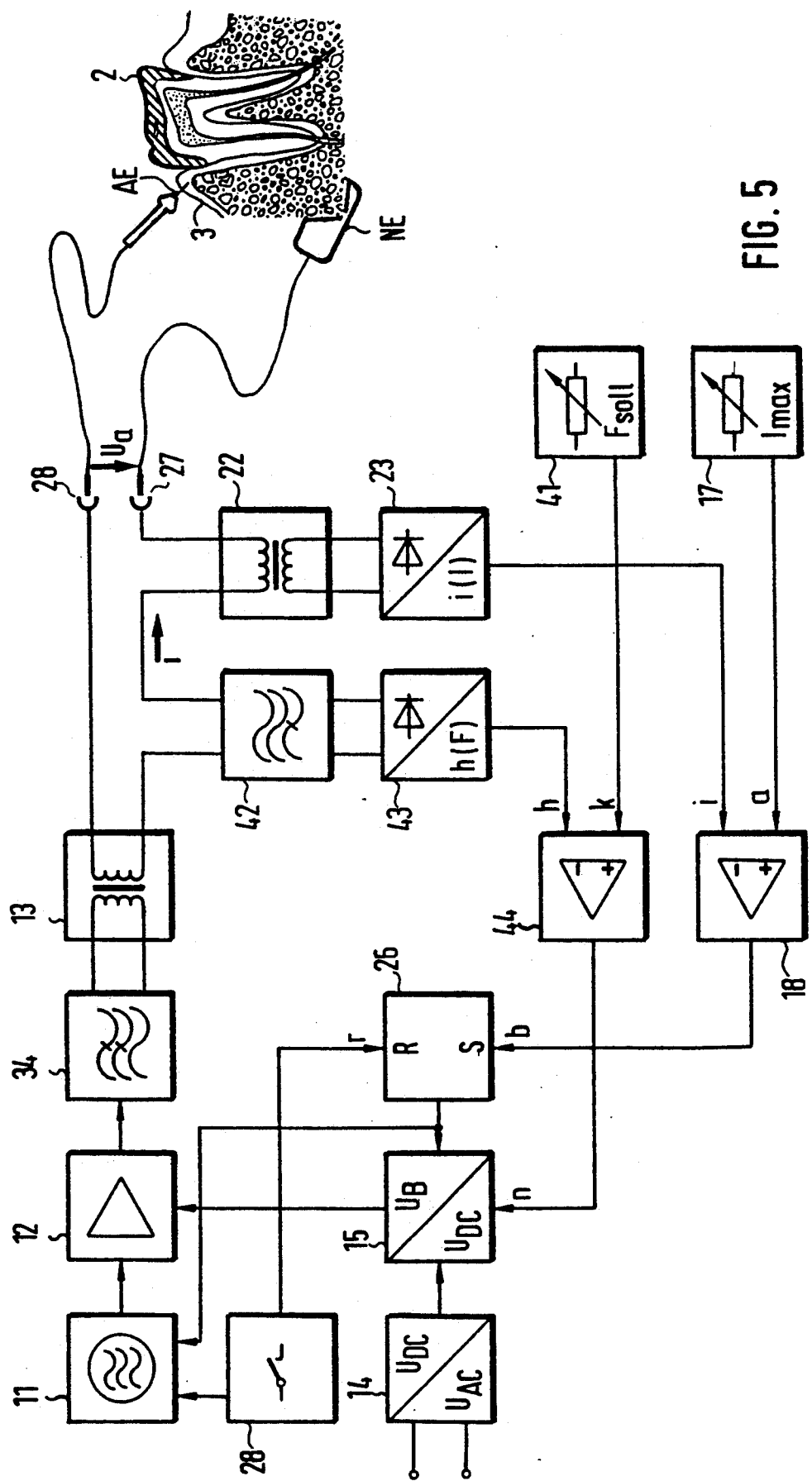

An embodiment of a high-frequency electrosurgery apparatus with automatic regulation of the HF output voltage $U_a$, with the amplitude of that alternating voltage being, for example, pulse-modulated will now be described with reference to FIG. 5 which shows, as a circuit block diagram, a further embodiment of high-frequency electrosurgery apparatus according to the invention. The high-frequency generator of this embodiment corresponds basically to those known high-frequency electrosurgery equipments having automatic regulation of the intensity of an electric arc between active electrode and tissue, for example EP 0 219 568, consists of the components of kinds in themselves known, which are also known as functional elements in FIG. 3: high-frequency oscillator 11, high-frequency power amplifier 12, output transformer 13, and power supply 14 and 15. It differs from FIG. 3 by having a reference value signal source 41 for which the desired value of the intensity of the electric arc can be set as a reference value.

The automatic regulation of the electric arc is obtained in a known way by means of an arc sensor, consisting of frequency filter 42 and a rectifier 43, which delivers an electrical signal h which is proportional to the intensity of the electric arc between active electrode AE and tissue 3 of the patient. The signal h is supplied to a comparator 44, where it is compared with a reference value signal k of the reference value signal source 41. The output signal n of the comparator 44 is supplied in a suitable way to the power supply 15 for control of the operating voltage $U_b$ in such a fashion that the intensity F of the electric arc corresponds to the intensity $F_{ref}$ which is set in the reference value source 41. Here again it is desirable for the high-frequency generator to deliver a sinusoidal HF voltage to the output 27, 28 which is free of harmonics of the fundamental high frequency. For this purpose a low-pass filter 34 is interposed between the HF power amplifier 12 and the output transformer 13. The current limiting device and all other functions of this embodiment correspond basically to what is shown in FIG. 4 and described above. Elements 24 and 25 of FIG. 3 are omitted in FIG. 5 for essentially the same reason as they were omitted in FIG. 4, since the intensity of the electric arc, like the HF alternating voltage of FIG. 4 is not as a rule provided with amplitude modulation.

Figure 6:
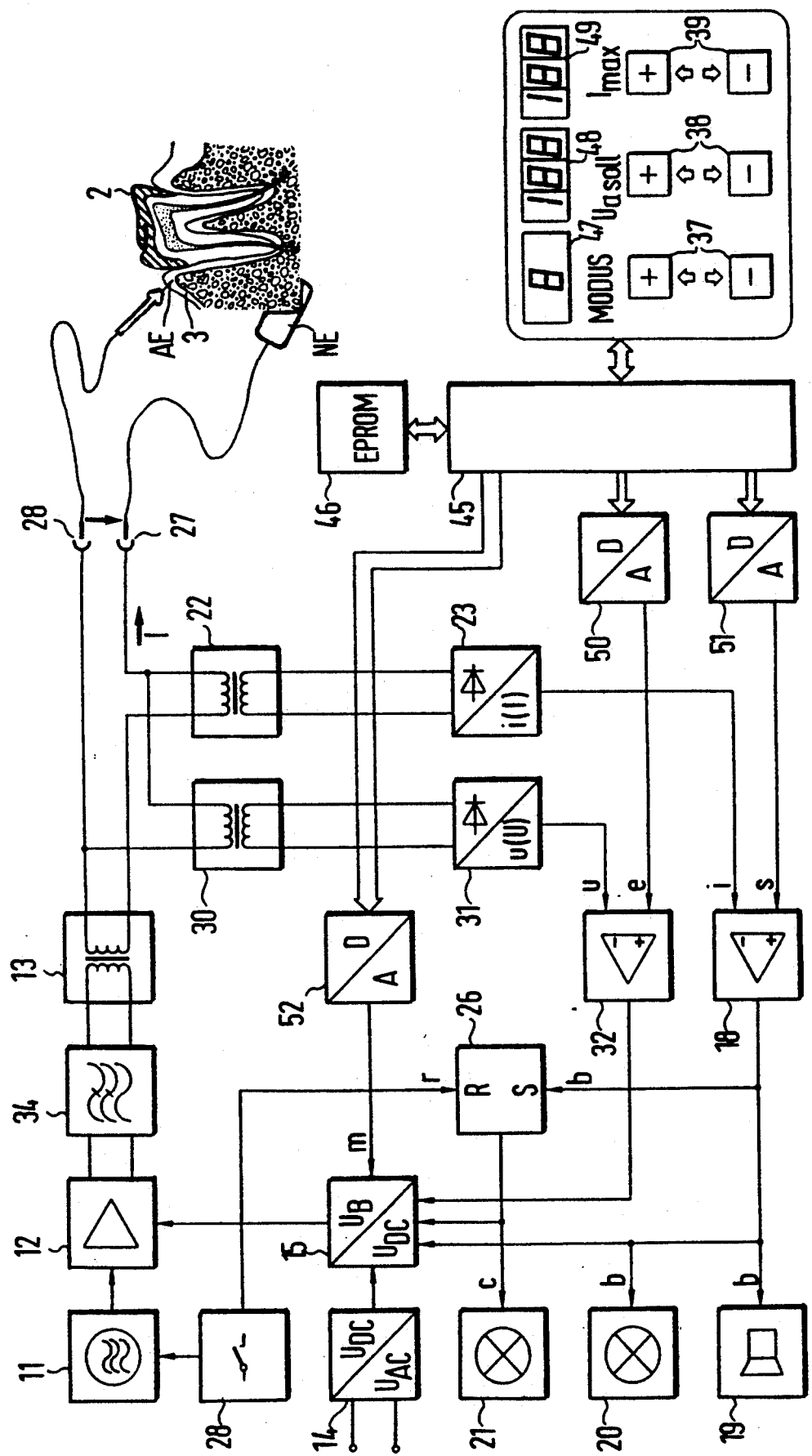

With reference to FIG. 6, there will now be described a further development of the embodiments shown in FIGS. 3, 4 and 5. In this case, a microcontroller or microprocessor 45 is used to provide for the setting of parameters, mode, HF output power $P_{HFref}$ or HF output voltage $U_{HFref}$, or intensity $F_{ref}$ of an electric arc between active electrode AE and tissue 3, as well as the maximum value $I_{max}$ of the current I and to produce these settings digitally from keyboard manipulations, for example by means of UP-DOWN keys 37, 38 and 39. Moreover, a parameter or other value set at any time can for example be shown on alphanumeric displays 47, 48 and 49.

The use of a microcontroller or microprocessor 45 in a high-frequency electrosurgery device according to the invention also has the advantage that the application of modes which require amplitude modulation of the HF output voltage $U_a$ and the amplitude modulation kind which is relevant to the selected mode can be automatically called out of a memory 46, for example an EPROM, and immediately furnished through a digital-to-analog converter 52 either to an amplitude modulator 25 as shown in FIG. 3 or to the power supply 15. The electric signal n in FIG. 6 is the modulation signal. This has the particular advantage that in cases of modes in which the amplitude modulation of the HF output voltage $U_a$ is involved, provision of the effective value for the electric signal i=f(I) is not performed by hardware, for example by a relatively expensive effective-value are rectifiers circuit, but rather by means of software provided for the microprocessor 45. For example it can be provided that the electric signal a=f($I_{max}$) is multiplied by a suitable form factor, for example the so-called crest factor C. By crest factor is meant the mathematical ratio of peak value to effective value of the alternating HF output voltage $U_a$, care being taken to assure that the integration time constant of the signal a must correspond to the period duration of the amplitude modulation by a whole-number multiple thereof.

The microprocessor 45 can thus provide, for every mode, a suitable form factor which is supplied to a digital-to-analog converter 51 that delivers an electric signal s. That signal corresponds to the product of the peak value of the signal a=f($I_{max}$) and the particular crest factor C of $U_a$.

According to the selected mode and/or selected HF output voltage $U_{a-ref}$ or the selected intensity $F_{ref}$ of the electric arc between active electrode AE and tissue 3, the microprocessor can also generate an electric signal e or k defined in each case by software, for which purpose, as is known, another digital-to-analog converter 50 is necessary.

Figure 7:
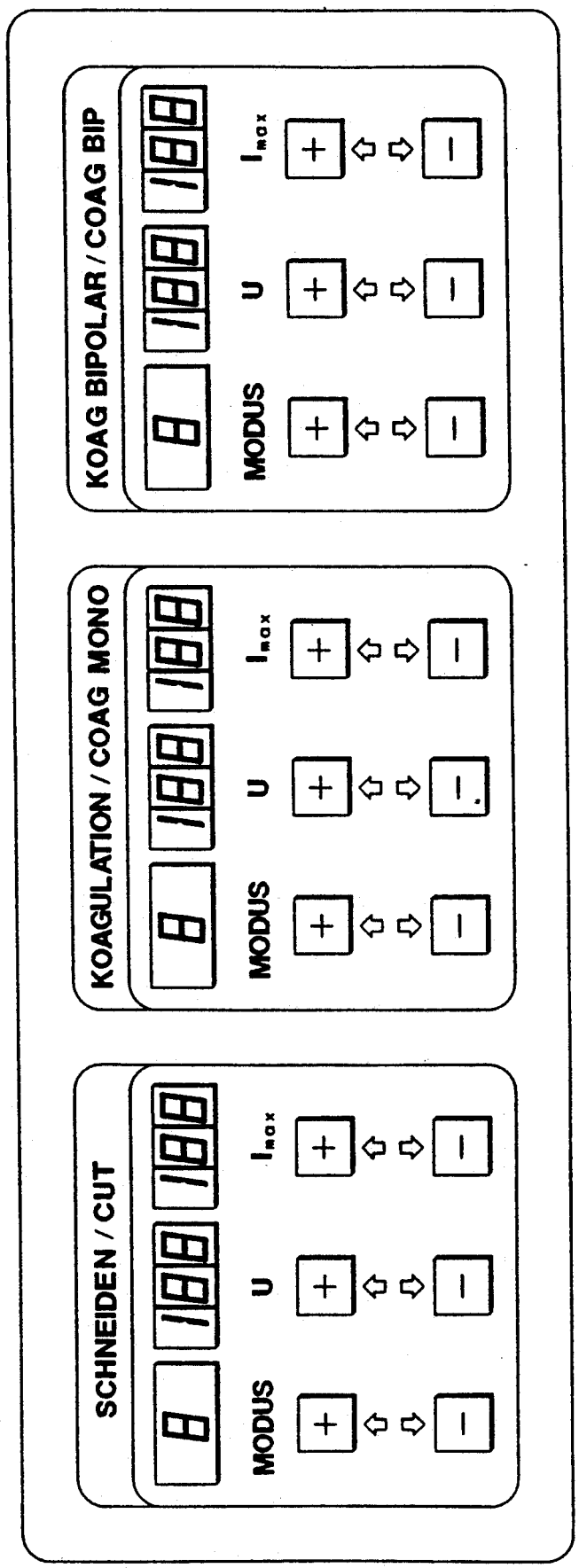
FIG. 7 is a front view of a front panel of a high-frequency electrosurgery apparatus according to the invention.

In FIG. 7 there is shown an example of a front panel of a high-frequency electrosurgery apparatus according to the invention. It is equipped, for example, with three function fields having captions respectively designating cutting, monopolar coagulation and bipolar coagulation. In each function field there are designated for example two well-known setting devices, those for mode and output voltage U. Mode signifies, in the case of cutting for example, the degree of coagulation or whether the cutting edges are to be of low coagulation or are to be edges of fully coagulating cuts. In the case of monopolar coagulation, the modes may be soft coagulation, forced coagulation or spray coagulation and for bipolar coagulation there may be for example microcoagulation or macrocoagulation. Here the symbol U signifies for example the HF output voltage, whether automatically regulated or not, or the intensity of an electric between active electrode and tissue, or the HF output power in watts.

In addition one or more function fields are equipped, in accordance with the invention, with a setting device for current limiting, at which there can be set the maximal value $I_{max}$ of the high-frequency alternating current of the application instrument of the apparatus.

Figure 8:
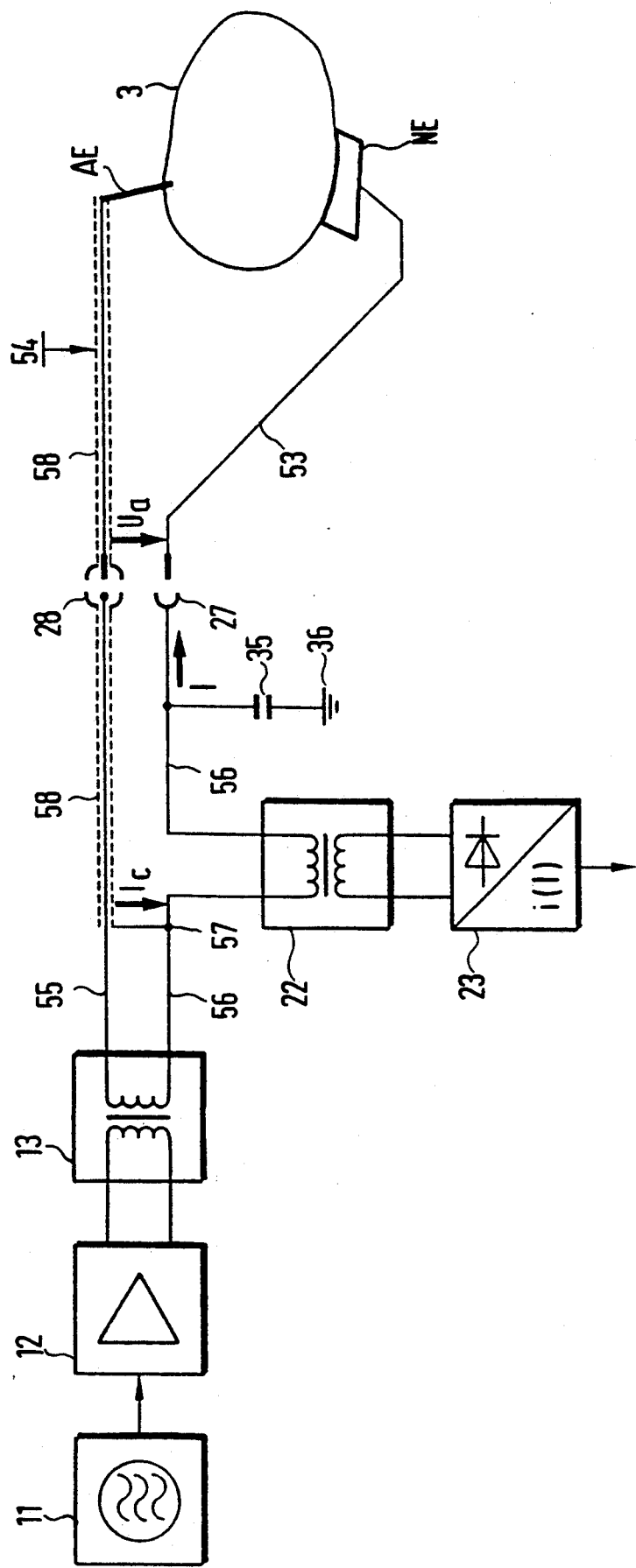
FIG. 8 is a partial representation of a circuit block diagram of a modified embodiment comparable with the embodiments shown in FIGS. 3-6.

As shown in FIG. 8, for avoiding the presence of capacitive currents between the conductors 55 and 56 as well as between the cables 53 and 54, both the conductor 55 and the cable 54 are electrically shielded. The shielding 58 of the conductor 55 and of the cable 54, connected together electrically in the output coaxial connector 28, needs to be connected electrically to the conductor 56 in such a way that the capacitive current $I_c$ does not flow through the HF current sensor 22, 23. The HF current sensor 22, 23 is therefore inserted between the connection terminal 57 of the conductor 56 and its output socket connector 27.

This solution is applicable both for high-frequency electrosurgery with so called floating output and for high-frequency electrosurgery with direct or capacitive grounding of a neutral electrode. In FIG. 8 a high-frequency electrosurgery apparatus with capacitive grounding is shown. The capacitor 35 is connected between the conductor 56 and the safety conductor potential 36 of the high-frequency electrosurgery apparatus. In apparatus with so-called floating output the capacitor 35 is omitted. In apparatus with direct grounding of the neutral electrode there is provided, instead of the capacitor 35, a d.c. conductive connection of low ohmic resistance.

Although the invention has been described with reference to particular illustrative examples, it will be recognized that variations and modifications are possible within the inventive concept. For example the remedial operation of the apparatus may be initiated when the $I_{max}$ current value is equalled or exceeded or only when it is exceeded, and the latter criterion is merely an obvious equivalent of a criterion of the first kind with a slightly higher value of $I_{max}$.

We claim:

1. A high frequency electrosurgery apparatus for cutting, coagulating, or simultaneously cutting and coagulating biological tissue comprising:
   a high frequency electric current generator having electric current outputs, electric current output parameters, and at least one mode of operation;
   electromechanical manually accessible setting means for setting at least one of said electric current output parameters wherein one of said electric current output parameters is a maximal current intensity;

manually positionable applicator electrodes means for applying high frequency electric current to biological tissue;

an electric current intensity limiting system connected to said electromechanical setting means for limiting said current intensity delivered to said applicator electrode means, said electric current limiting system including detecting means for detecting a current intensity equal to or exceeding said maximal current intensity in said applicator electrode means; and an alarm circuit connected to said detecting means responding to said current intensity equal to or exceeding said maximal current intensity in said detecting means for activating at least one of two means of said alarm circuit:

(a) means for shutting off said high frequency electric current generator;

(b) means for producing a warning signal.

2. A high frequency electrosurgery apparatus for cutting, coagulating, or simultaneously cutting and coagulating biological tissue comprising:

a high frequency electric current generator having a readily selectable plurality of modes of operation, having a plurality of current outputs and current output parameters associated with each of said modes of operation, and further comprising a power supply component;

electromechanical parameter setting means for setting said plurality of current output parameters wherein one of said current output parameters is a maximal current intensity and further comprising a manual setting means for setting said current output parameters;

manually positionable applicator electrode means for applying high frequency electric current to biological tissues;

electric current intensity limiting means for limiting said current intensity delivered to said applicator electrode means; said electric current intensity limiting means further comprising detecting means for detecting a current intensity equal to or exceeding said maximal current intensity in said applicator electrode means; and alarm means for responding to detection of said current intensity equal to or exceeding said maximal current intensity in said detecting means and for activating at least one of two means:

(a) means for shutting off said high frequency electric current generator, said power supply component, or both, (b) means for producing a warning signal.

3. The high frequency electrosurgery apparatus of claim 2, wherein said detecting means further comprises:

(a) current intensity monitor means which generates a first electric signal which is proportional to the current intensity in said applicator electrode means;

(b) electric signal source means for producing a second electric signal which is proportional to said maximal current intensity; and (c) comparator means for comparing said first electric signal to said second electric signal to determine the ratio of the two electric signals and generating a control signal dependent thereon; and said alarm means further comprising a control means for supplying said control signal to activate said means for shutting off, to activate said means for producing a warning signal, or to limit said current intensity to said maximal current intensity.

4. The high frequency electrosurgery apparatus of claim 3 wherein said current intensity monitor means contains a phase selective rectifier.

5. The high frequency electrosurgery apparatus of claim 4, wherein said high frequency electric current generator further comprises an output transformer;

said applicator electrode means further includes an active electrode, a neutral electrode, and a cable; and said cable comprises a metallic electric field shielding connected to a conductor of said neutral electrode.

6. The high frequency electrosurgery apparatus of claim 4 further comprising:

display means for displaying said maximal current intensity.

7. The high frequency electrosurgery apparatus of claim 6, wherein:

said electromechanical parameter setting means further comprises manual means for selecting one of said modes of operation;

said manual setting means for setting said maximal current intensity further comprises a plurality of said manual setting means for each of said modes of operation; and said electric current intensity limiting means includes a plurality of said electric current intensity limiting means for each mode of operation.

8. The high frequency electrosurgery apparatus of claim 7 wherein:

said comparator means further comprises a delay circuit means for delaying said control signal to said alarm means.

9. The high frequency electrosurgery apparatus of claim 6 wherein:

said comparator means further comprises a delay circuit means for delaying said control signal to said alarm means.

10. The high frequency apparatus of claim 4 which further comprises:

reference value signal means for setting a voltage for an output of said high frequency electric current generator.

11. The high frequency electrosurgery apparatus of claim 4 wherein:

said comparator means further comprises a delay circuit means for delaying said control signal to said alarm means.

12. The high frequency electrosurgery apparatus of claim 3, wherein said high frequency electric current generator further comprises an output transformer;

said applicator electrode means further includes an active electrode, a neutral electrode, and a cable; and said cable comprises a metallic electric field shielding connected to a conductor of said neutral electrode.

13. The high frequency electrosurgery apparatus of claim 3 further comprising:

display means for displaying said maximal current intensity.

14. The high frequency electrosurgery apparatus of claim 13, wherein:

said electromechanical parameter setting means further comprises manual means for selecting one of said modes of operation;

said manual setting means for setting said maximal current intensity further comprises a plurality of said manual setting means for each of said modes of operation; and said electric current intensity limiting means includes a plurality of said electric current intensity limiting means for each mode of operation.

15. The high frequency electrosurgery apparatus of claim 13 wherein:

said comparator means further comprises a delay circuit means for delaying said control signal to said alarm means.

16. The high frequency apparatus of claim 3 which further comprises:

reference value signal means for setting a voltage for an output of said high frequency electric current generator.

17. The high frequency electrosurgery apparatus of claim 16 wherein:

said comparator means further comprises a delay circuit means for delaying said control signal to said alarm means.

18. The high frequency electrosurgery apparatus of claim 3 wherein:

said comparator means further comprises a delay circuit means for delaying said control signal to said alarm means.

19. The high frequency electrosurgery apparatus of claim 2 wherein, said high frequency electric current generator further comprises an output transformer;

said applicator electrode means further includes an active electrode, a neutral electrode, and a cable; and said cable comprises a metallic electric field shielding connected to a conductor of said neutral electrode.

20. The high frequency electrosurgery apparatus of claim 2 further comprising:

display means for displaying said maximal current intensity.

21. The high frequency electrosurgery apparatus of claim 20, wherein:

said electromechanical parameter setting means further comprises manual means for selecting one of said modes of operation;

said manual setting means for setting said maximal current intensity further comprises a plurality of said manual setting means for each of said modes of operation; and said electric current intensity limiting means includes a plurality of said electric current intensity limiting means for each mode of operation.

22. The high frequency apparatus of claim 2 further comprises:

reference value signal means for setting a voltage at an output of said high frequency electric current generator.

* * * * *